United States Patent [19]

Sekhar et al.

[11] Patent Number: 4,928,705

[45] Date of Patent: May 29, 1990

[54] ACOUSTIC ANEURYSM DETECTOR AND ASSOCIATED METHOD

[75] Inventors: Laligam N. Sekhar; Robert J. Scalbassi; Mingui Sun, all of Pittsburgh, Pa.; Jacob F. Wasserman, Knoxville, Tenn.

[73] Assignees: University of Pittsburgh of the Commonwealth System of Higher Education, Pittsburgh, Pa.; University of Tennessee Researach Corporation, Knoxville, Tenn.

[21] Appl. No.: 130,108

[22] Filed: Dec. 8, 1987

[51] Int. Cl.$^5$ .............................................. A61B 5/02
[52] U.S. Cl. .................................................. 128/773
[58] Field of Search ............................... 128/773, 644

[56] References Cited

U.S. PATENT DOCUMENTS

| 2,549,836 | 4/1951 | McIntyre et al. | 128/773 X |
| 3,076,870 | 2/1963 | Jones, Jr. | 179/1 |
| 3,181,528 | 5/1965 | Brackin | 128/2 |
| 3,773,033 | 11/1973 | Rodbard et al. | 128/2.06 R |
| 4,008,711 | 2/1977 | Olinger et al. | 128/2 K |
| 4,226,248 | 10/1980 | Manoli | 128/773 |
| 4,438,772 | 3/1984 | Slavin | 128/715 |
| 4,510,944 | 4/1985 | Porges | 128/687 |
| 4,561,447 | 12/1985 | Kawamura et al. | 128/687 |
| 4,672,977 | 6/1987 | Kroll | 128/773 X |

OTHER PUBLICATIONS

Ferguson, G. G., Direct Measurement of Mean And Pulsatile Blood Pressure at Operation in Human Intracranial Saccular Aneurysms, J. Neurosurg., vol. 36, pp. 560-563, (1972).

Olinger et al., Electronic Stethoscope for Detection of Cerebral Aneurysm, Vasospasm and Arterial Disease, Surg. NNeurol., vol. 8, pp. 298-312, (1977).

Kosugi et al., Sonic Detection of Intracranial Aneurysm and AVM, Stroke, vol. 14, No. 1, pp. 37-42, (1983).

Sekhar et al., Noninvasive Detection of Intracranial Vascular Lesions Using an Electronic Stethoscope, J. Neurosurg., vol. 60, pp. 553-559, (1984).

Wasserman, The Acoustic Detection of Cerebral Aneurysms, Doctoral Dissertation, (1975).

Primary Examiner—Francis Jaworski
Attorney, Agent, or Firm—Arnold B. Silverman

[57] ABSTRACT

An acoustic aneurysm detector is disclosed which is comprised of hydrophone sensors in contact with a patient for receiving sound emanating from the patient and converting the sound into responsive or related electrical signals, an electronic unit for converting the responsive electrical signals into processed electrical signals and a computer having software which is operatively associated with the electronic unit for receiving the processed electrical signals and for providing an indication of the frequency of the sound over a specified time range. An associated method is also disclosed.

32 Claims, 13 Drawing Sheets

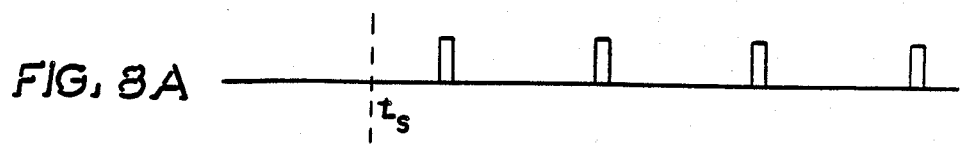
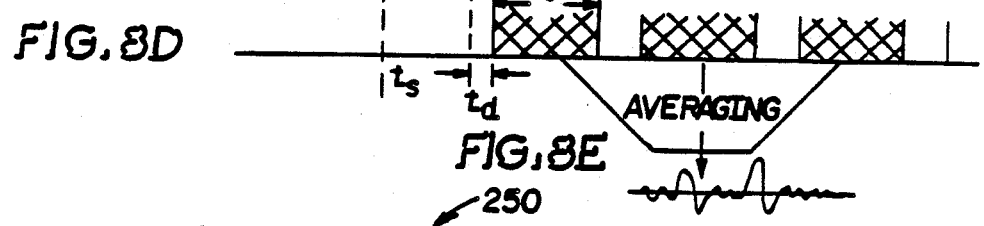
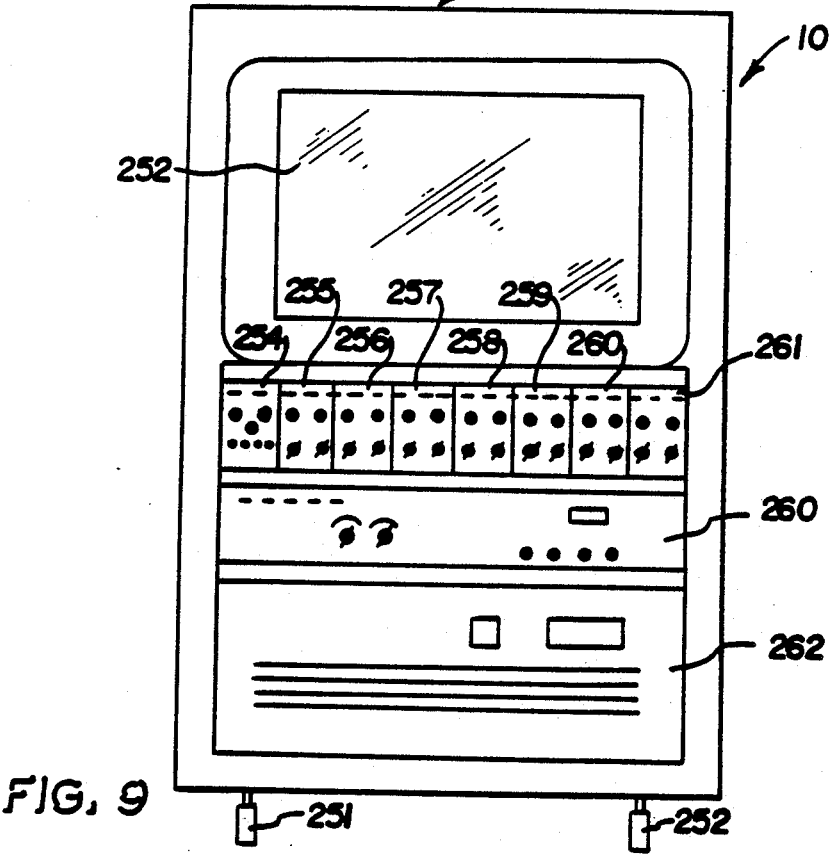

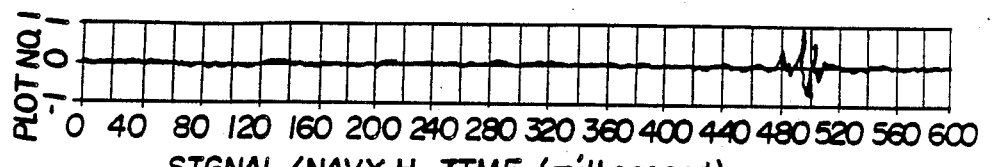
FIG. 17A
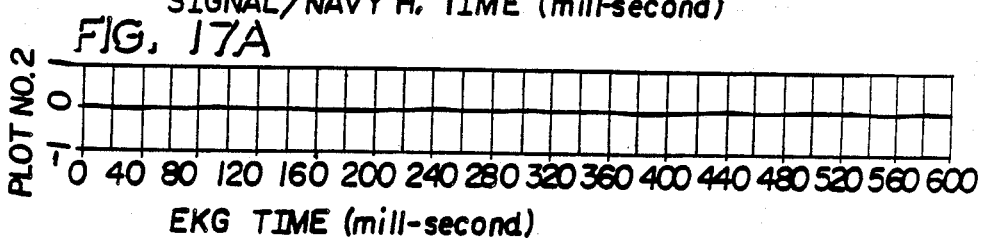
FIG. 17B
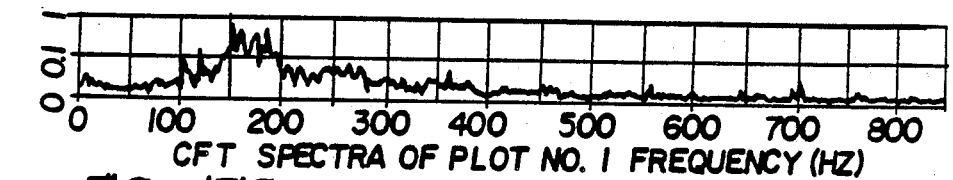
FIG. 17C
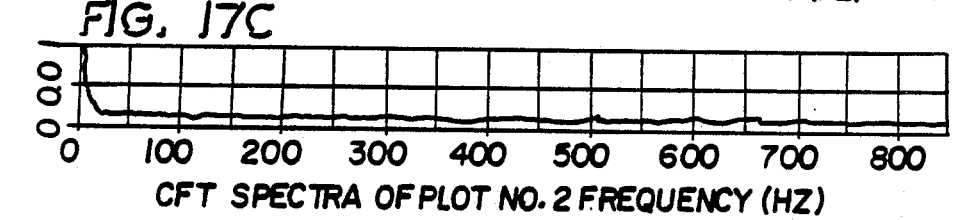
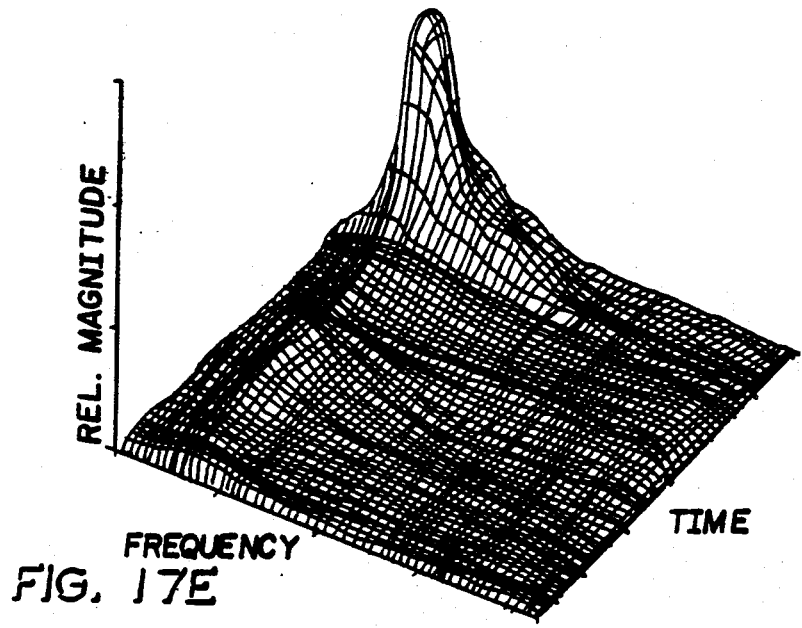
FIG. 17E

BAND RANGE (HZ): 0.0-85.3 ENERGY RATIO =

BAND RANGE (HZ): 85.3-170.7 ENERGY RATIO = 24.7%

BAND RANGE (HZ): 170.7-258.0 ENERGY RATIO = 21.3%

BAND RANGE (HZ): 256.0-341.3 ENERGY RATIO = 13.3%

BAND RANGE (HZ) 341.3-428.7 ENERGY RATIO = 8.8%

BAND RANGE (HZ): 426.7-512.0 ENERGY RATIO = 6.8%

BAND RANGE (HZ): 512.0-59.3 ENERGY RATIO = 5.8%

BAND RANGE (HZ): 507.3-682.7 ENERGY RATIO = 4.6 %

BAND RANGE (HZ): 682.7-768.0 ENERGY RATIO = 3.9%

BAND RANGE (HZ): 788.0-453.3 ENERGY RATIO = 4.2%

ACOUSTIC ANEURYSM DETECTOR AND ASSOCIATED METHOD

BACKGROUND OF THE INVENTION

1. Field Of The Invention:

This invention relates to an apparatus and method which noninvasively detects the existence of cerebral aneurysms in humans and more specifically to an improved system having multiple channels for detecting sound waves created by aneurysms and equipment for analyzing the sound waves.

2. Description Of The Prior Art:

An aneurysm is an abnormal outpouching of the wall of a blood vessel which leaves it vulnerable to enlargement or rupture with severe intracranial hemorrhage. Ruptured aneurysms are a serious clinical problem.

It has been estimated that approximately 28,000 persons suffer a subarachnoid hemorrhage from a ruptured aneurysm annually in North America. The problem is serious because over fifty percent of these patients die and about fifteen percent are severely disabled.

If an aneurysm is detected prior to rupture, it can frequently be treated by the surgical procedure of clip occlusion. This surgery can be performed with a very low rate of complication with an excellent outcome. Once the aneurysm ruptures, however, the clinical condition of the patient deteriorates severely due to the major brain injury which occurs at the time of rupture. Under these conditions, the morbidity and mortality are high in spite of modern advances in treatment.

Up to 60% of individuals who suffer subarachnoid hemorrhage have been reported to exhibit "warning signs" prior to aneurysmal rupture. However, many of the symptoms are nonspecific such as headache, occular pain, and nausea and therefore frequently have been mistaken for a viral illness or for a minor headache. The only way to make a real impact on the outcome of the disease would be to diagnose the problem in individuals exhibiting these vague warning symptoms, or in asymptomatic individuals, by screening populations at risk with noninvasive tests.

There are several known methods for detecting aneurysms before they rupture. One method is angiography. However, this invasive procedure entails expensive hospitalization, trauma and patient risk and therefore is not suited for investigating vague, prodromal symptoms even though those symptoms might precede fatal aneurysm rupture. Thus, a physician faced with possible aneurysm warning signs must judge whether the symptoms warrant the trauma, and expense, of an angiogram.

Ferguson, in *J. Neurosurg* 36:560–563 (1972), suggested detecting aneurysmal signals by recording sounds from aneurysms exposed at operations using a cardiac phono-catheter which recorded musical sounds from lesions.

Kosugi et al., in Stroke 14 (1) 37–42 (1983), disclosed the use of a "cement wall microphone" (contact accelerometer) in contact with the cranium and the teeth in an attempt to detect aneurysms.

Sekhar and Wasserman, in *J. Neurosurg* 60:553–559 (1984), disclosed the use of a a Horn-Coupled microphone for non-invasive detection of aneurysms.

Olinger and Wasserman, in Surg. Neurol. 8:298-312 (1977), disclosed the use of air microphone devices for noninvasive detection of aneurysms.

Several United States patents disclose noninvasive aneurysm monitoring techniques. U.S. Pat. No. 4,008,711 discloses a standard electronic low-noise microphone housed in an isolation chamber which detects sound waves from the patient's eyes. These sound waves are converted into an electrical signal which is passed through a final filter to a computer having a Fourier analysis capability. The computer analyzer is disclosed to be a Fourier Analyzer which can output data to a standard CRT or Plotter.

U.S. Pat. No. 4,226,248 discloses a phonocephalographic device having a pair of ear insertable microphones that can detect sounds from the surface and cavities of the head. Amplified signals are processed through a frequency analyzer and can go then to a chart recorder or oscillator.

Despite these known devices, there remains a need for an acoustic aneurysm detector that is designed to more effectively record and analyze the data to aid in the detection of human aneurysms before they rupture.

SUMMARY OF INVENTION

The acoustic aneurysm detector of the invention has met the above-described need. The detector is comprised of hydrophone sensor means in contact with a patient for receiving sound emanating from the patient and converting the sound into responsive or related electrical signals, electronic means for converting the responsive electrical signals into processed electrical signals and analysis means operatively associated with the electronic means for receiving the processed electrical signals for providing an indication of the frequency of the sound over a specified time range.

The method of the invention involves providing the detector as described hereinabove, placing the hydrophone sensor means on the patient for receiving said signals from the patient, converting the sound by the hydrophone sensor means to responsive electrical signals, amplifying and filtering said responsive electrical signal by electronic means to create processed electrical signals, delivering the processed electrical signal to analysis means and outputting an indication of the frequency of the sound over a specified time range by using said analysis means.

It is an object of the invention to provide an apparatus to effectively detect the presence of aneurysms in humans by an acoustic method.

It is a further object of the invention to employ sensitive hydrophones as sensors in order to provide an improved signal to noise ratio.

It is a further object of the invention to provide a detector that provides correction for the 60 dB difference when a fluid medium signal is converted to an air medium signal.

It is a further object of the invention to provide a unique eight-channel system that better validates the authenticity of the aneurysmal signal.

It is a further object of the invention to provide a unique eight-channel system with seven channels dedicated to detection of the aneurysm, that aids in better understanding of the effect of specific physiological parameters on the aneurysmal signal itself.

It is a further object of the invention to provide a detector that has a band-pass filter which provides a method of filtering out undesired interrupting signals.

It is a further object of the invention to provide an improved method of data analysis for aneurysmal sounds.

It is a further object of the invention to provide such a system which has improved sensitivity and specifity in the detection of aneurysms.

These and other objects of the invention will be fully understood from the following description of the invention with reference to the illustrations appended to this Application.

BRIEF DESCRIPTION OF THE DRAWINGS

FIGS. 8(A), 8(B), 8(C), 8(D) and 8(E) show a series of representations of a recorded signal.

FIG. 9 shows a front elevational view of the detector mounted in a portable cart.

FIGS. 17(A), 17(B), 17(C), 17(D), 17(E), 17(F), 17(G), 17(H), 17(I), 17(J) 17(K), 17(L), 17(M), 17(N), and 17(O) show a number of plots and a spectrogram of the aneurysmal signal with full analysis from a patient with a large cerebral aneurysm at the junction of the vertebral and basilar arteries.

DESCRIPTION OF THE PREFERRED EMBODIMENT

As used herein, unless a specific usage provides a specific indication to the contrary, "patient" refers not only to human beings, but also to other members of the animal kingdom.

An aneurysm produces an aneurysm-characteristic sound which can be noninvasively recorded and analyzed to distinguish it from other body sounds. The method of the preferred embodiment includes detecting the probable existence of cerebral aneurysms by noninvasively monitoring body sounds over predetermined areas of the head and analyzing the sounds to determine the existence of an aneurysm-characteristic sound.

Figures 1, 2:
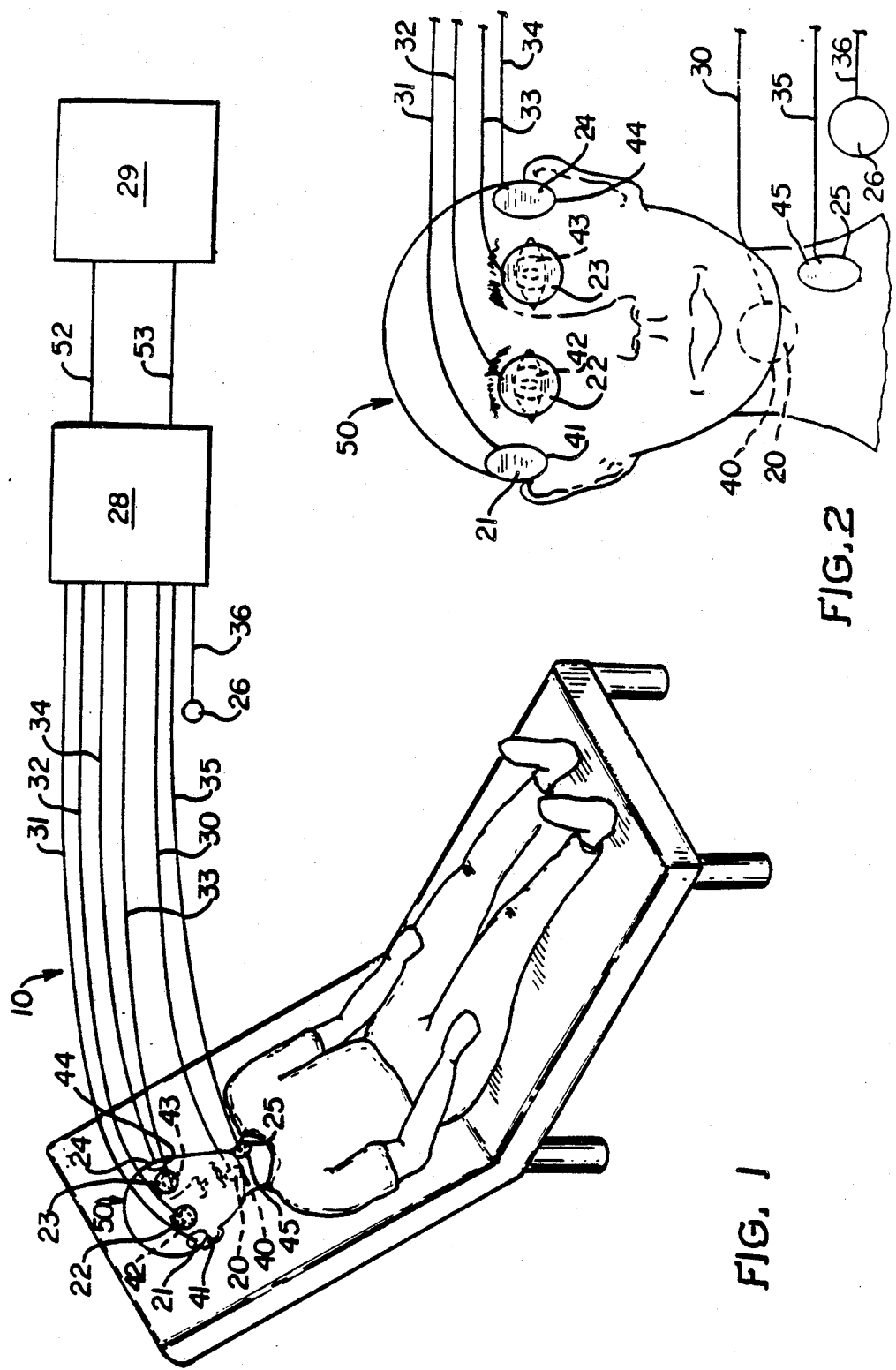
FIG. 1 is a schematic illustration of the acoustic aneurysm detector of the present invention connected to a reclining patient.
FIG. 2 shows a detailed view of a type of sensor arrangement on the head of the patient.

As can be seen in FIGS. 1 and 2, the acoustic aneurysm detector 10 consists of a plurality (preferably seven) of hydrophonic (fluid coupled microphones) sensors 20-26, supporting electronics unit 28 operatively associated therewith and a computer 29. The aneurysm characteristic sound is received by and converted to responsive electrical signals by the hydrophone sensors 20-26. The intensity of the sound will provide a corresponding responsive electrical signal. This responsive electrical signal is carried by the lead wires 30-36 associated with the respective sensors 20-26 to electronic means 28.

The electronic means 28 amplifies and filters the responsive electrical signal into a processed electrical signal which is input into the analysis means 29 (preferably a computer) by wire leads 52 and 53.

As can best be seen in FIG. 2, the sensors are preferably placed as follows. Sensor 20 is placed in contact with the foramen magnum area (behind the patient's head) 40 of the patient's head 50. Sensors 21 and 24 are placed in contact with the temporal regions 41 and 44, respectively, of the patient's head 50 and sensors 22 and 23 are placed over the eyes 42 and 43 of the patient in contact with the exteriors of the eyelids. Sensor 25 is placed on the neck 45 of the patient where it can monitor biological noise. Sensors 20-25 are preferably coupled to the patient by using EKG gel and a suction cup as is well known to those skilled in the art. Biological noise refers to potentially interfering sounds emitted by portions of the body other than those to which sensors 20-24 are secured such as sounds of breathing, heart sounds, eye blinks, and digestive system sounds, for example. Sensor 26 is placed in the room in which the test is performed to monitor room noise, and if desired may conveniently be secured to the exterior of the housing of the electronics means 28.

The sensors 20-24 then, respectively, receive body sounds from the foramen magnum area 40, temporal region 41, eyes 42, 43, and temporal region 44. The sensors 20-24 are secured by any desired means at the respective locations in intimate relationship in order to facilitate effective transfer of sound from the areas of the head which are being monitored.

It is preferred that the temporal region sensors 21 and 24 be placed on the thinnest region of the skull. This region may be determined by using a commercially available transcranial doppler machine such as *Eden Modizinishe Elektronik* Mode TC 2-64. Once this region is determined, the temporal region sensors 21 and 24 can be placed thereon for most effective results.

The sensors 20-24 pick up sound which is triggered by the R-wave of the electrocardiogram (EKG) and is viewed for acceptance or rejection by the technician. The room noise is also preferably monitored simultaneously by sensor 26 for comparison. Following the actual test, the analysis of the data can be made and the existence or nonexistence of an aneurysm is determined.

The sensors 20-26 are preferably fluid coupled microphones (hydrophones) which are well known to those skilled in the art. Preferably, all of the sensors 20-26 are identical or generally identical to each other.

During the test, the patient is preferably in a reclining position and is asked to hold his or her breath and to close his or her eyes during the active portion of the test.

Figure 3A:
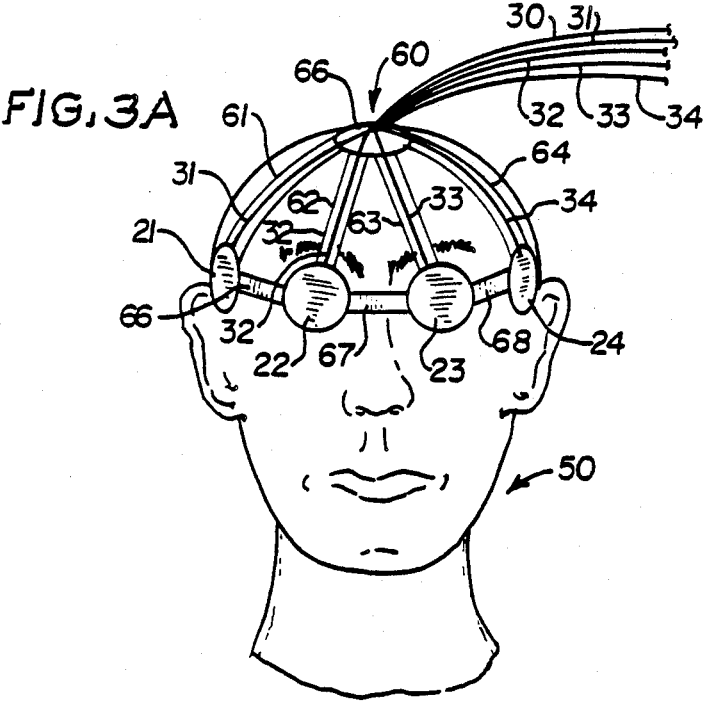
FIGS. 3(A), 3(B) and 3(C) show front, right side and left side elevational views, respectively, of the hydrophonic sensors used in the invention mounted in a specially designed helmet that fits over the patient's head.
Figure 3B:
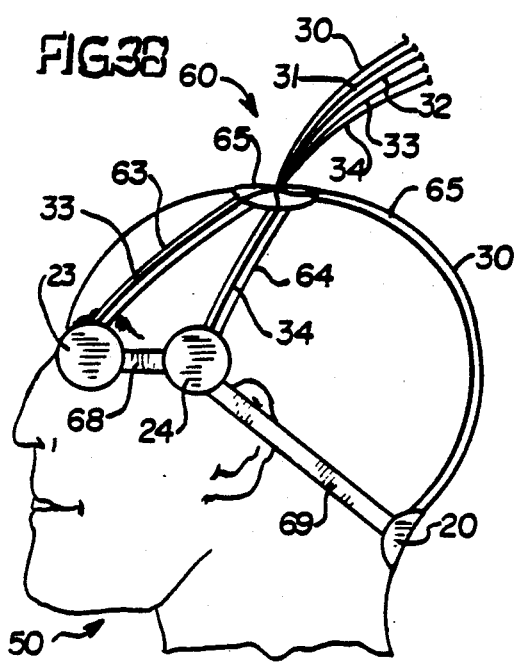
Figure 3C:
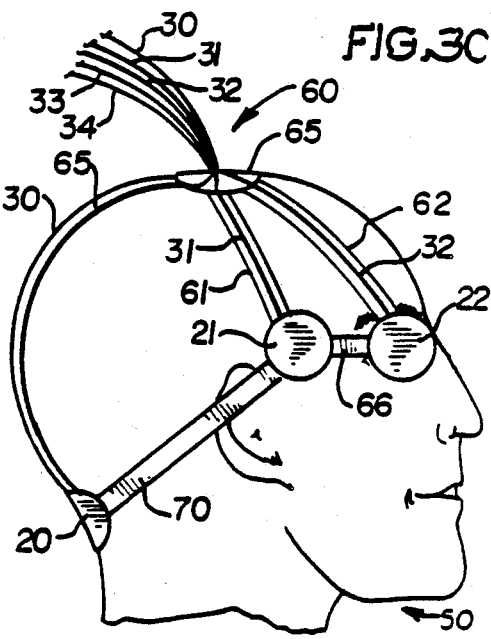

FIGS. 3(A), 3(B) and 3(C) show optional helmet means 60 for holding the sensors 21-25 in intimate contact with the patient's head 50. The helmet means 60 consists of five spokes 61–65 which emanate from a central hub 66. The hub 66 preferably receives the separate leads 30–34 from the respective sensors. The leads 30–34 extend towards the electronic unit 28 as shown in FIG. 1.

Disposed at the free ends of the spokes 61–64 are the respective sensors 21–25. For further support, the sensors 21–25 are joined, respectively, by a series of connecting bridges 66–70. The spokes 61–64 and connecting bridges 66–70 may be resilient or otherwise adjustable to fit different sized patient's heads. This adjustability can be accomplished by other means well known such as by a tongue and groove apparatus and a suitable clamping means such as a screw. The helmet 60 can also be adjusted so as to maintain intimate contact with the patient's head by spring biased means.

The supporting electronics 28 may consist of an eight-channel system. One channel is for reception of the EKG R-wave and seven channels are designed for sound related signal reception. The signal channels include five channels associated with sensors 20–24 for receiving sound related to cerebral sound recordings, one channel associated with sensor 26 for receiving sound relating to room noise, and one auxiliary channel associated with sensor 25 for receipt of sound related to biological noise.

The seven signal channels preferably have identical electrical characteristics and, therefore, can be assigned to different sensors on different locations arbitrarily. The preferred arrangement of sensors was described hereinbefore and is shown in FIG. 2. With this arrangement, the attenuation of sound that passes through the skull can be reduced.

The distances between the sensors 20, 21, 22, 23, and 24 and the aneurysmal signal source are much shorter than the distances between sensors 25 and 26 and their respective sound sources. On the other hand, the distances between noise sources, such as heart sound source, and respiratory sound source are not very different. As a result, by adaptive subtraction, the combination of recordings from sensors 25 and 26, (with proper weighting), from the recordings of sensors 20–24, the undesired interfering noise can be virtually completely removed, leaving the aneurysmal signal only slightly attenuated. A least mean square algorithm for interference cancelling, using the Adaptive Linear Combiner is preferably used, as was disclosed in Widrow's *Adaptive Signal Processing* 1985 pp. 302–361.

The eighth channel, the EKG channel, is designed differently from the above mentioned seven channels. It is used primarily for producing a trigger signal at the time of the R-wave, corresponding to the peak of the EKG.

Figure 4:
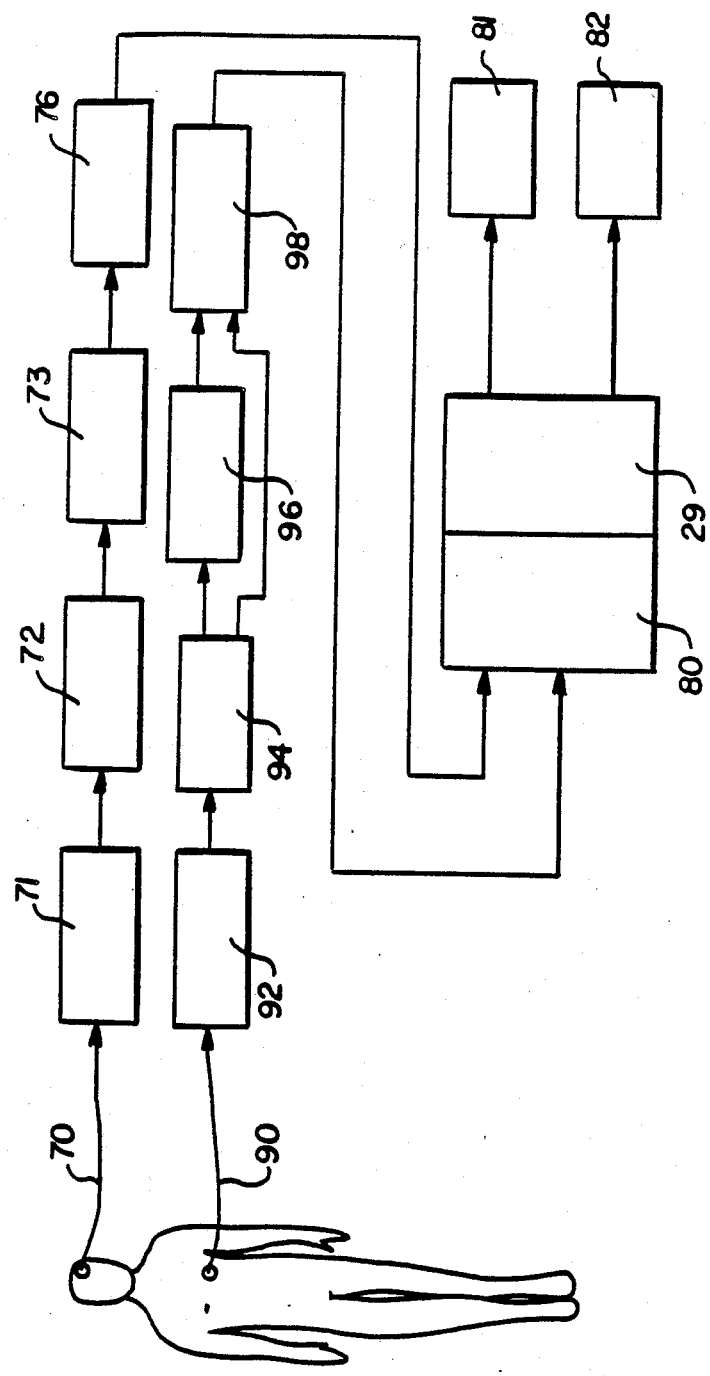
FIG. 4 is a schematic view of a patient and a block diagram of a portion of the acoustic aneurysm detection system.

FIG. 4 shows a block diagram of the acoustic aneurysm detector system, including the computer 29. As can be seen in FIG. 4, the signal channel 70 consists of hydrophone sensors 71 (representing the seven sensors 20–26) which receive sound and emit responsive related electrical signals which pass through a pre-amplifier 72 to a band-pass filter 74 and a second amplifier 76. The second amplifier 76 outputs a processed electrical signal to the analog to digital converter 80 which signal is in turn delivered to the computer 29 which further processes the signal and outputs data to a visual display 81 and/or hardcopy printer 82.

The EKG channel 90 as shown in FIG. 4 consists of a differential amplifier 92, a 60 Hz Notch Filter 94, a Peak-Value detector and scalar 96, and a comparator and differentiator 98. The EKG channel signal 90 after this processing is also input into the computer 29 for data analysis.

Figure 5:
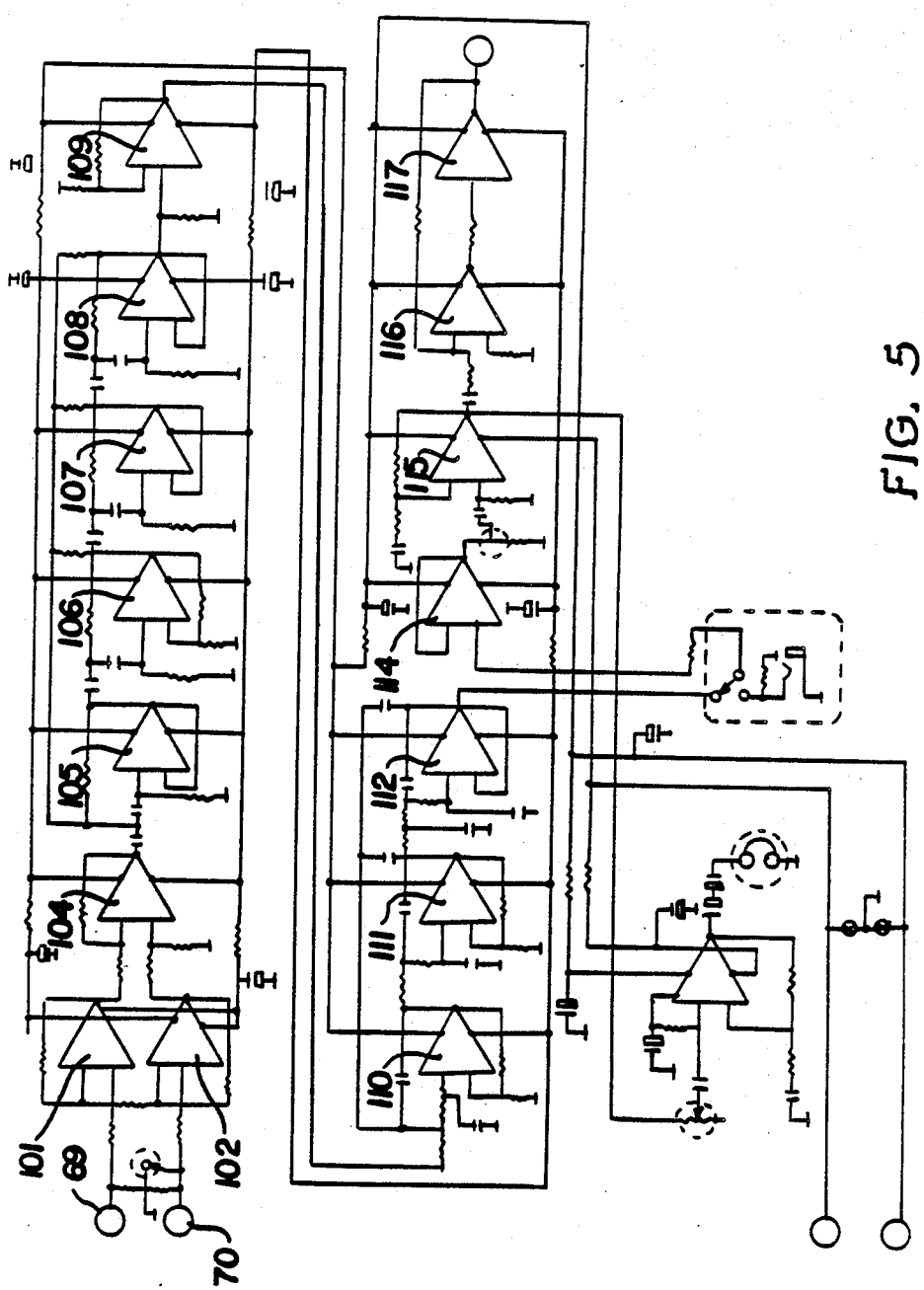
FIG. 5 shows a form of circuit for the acoustic aneurysm detector signal channel unit channel.
Figure 6:
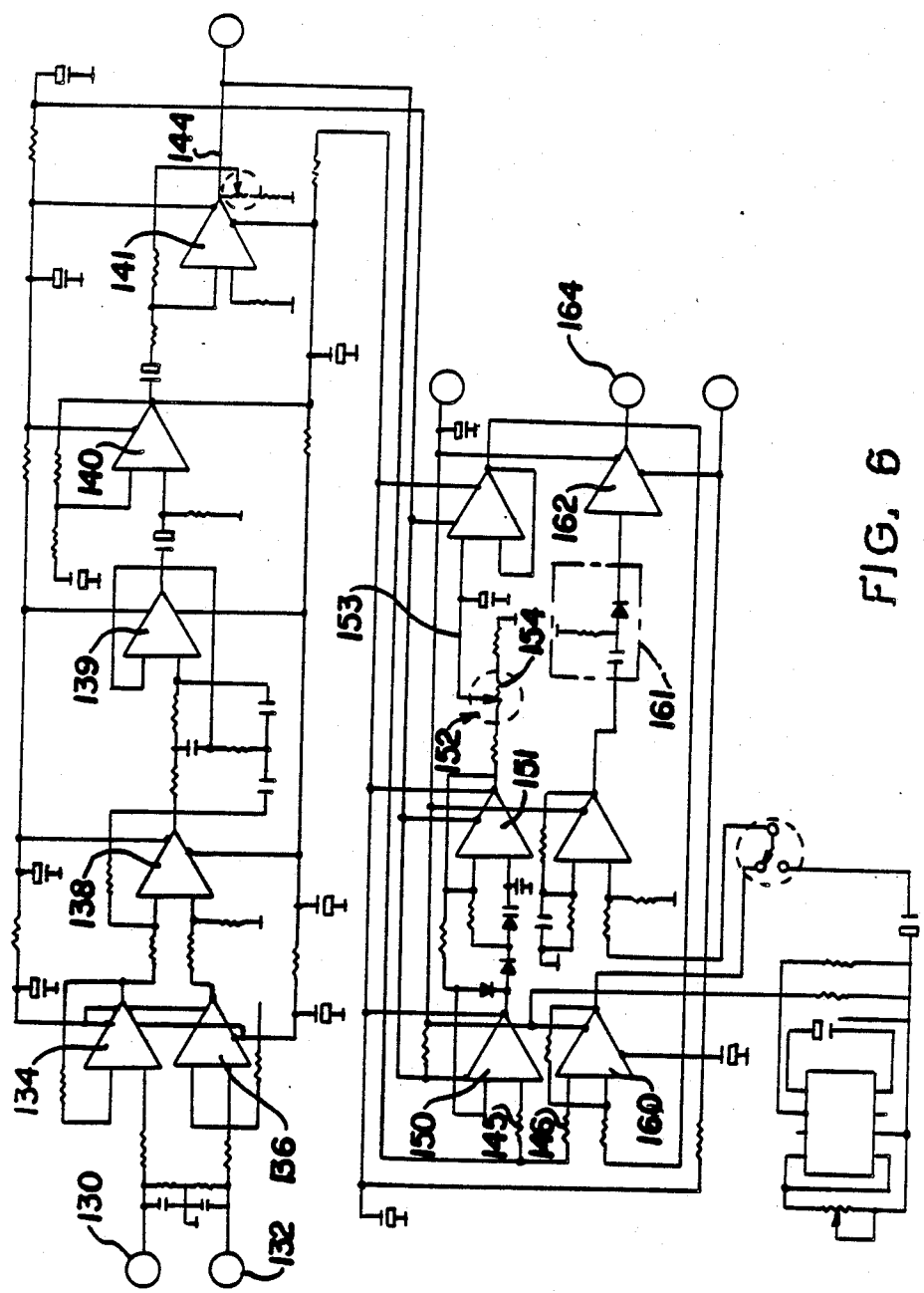
FIG. 6 shows a form of circuit diagram of the EKG channel unit.
Figure 7:
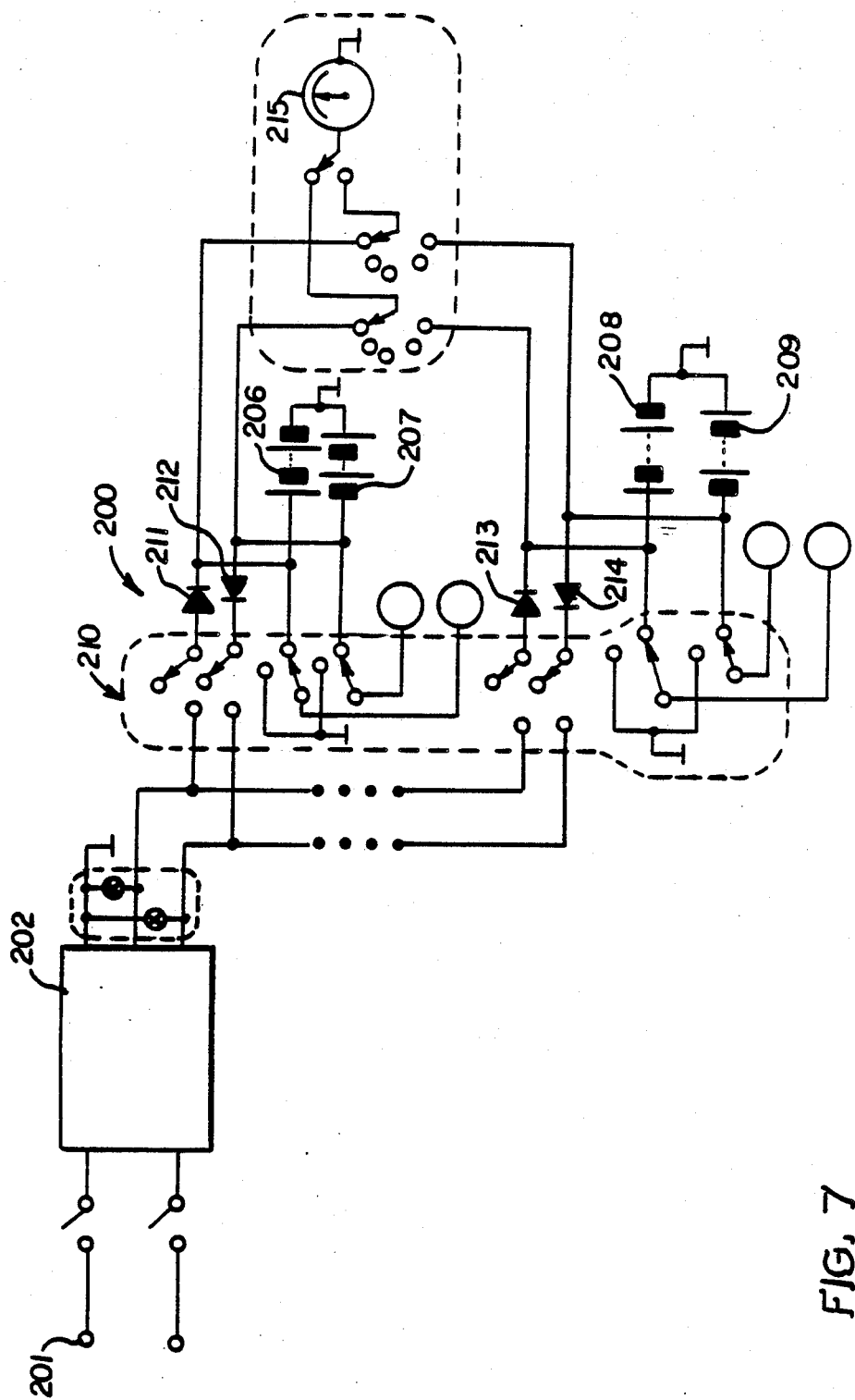
FIG. 7 is a circuit diagram of the power supply for the acoustic aneurysm detector.

FIGS. 5, 6, and 7 provide detailed schematics of supporting electronics, including the signal channel unit, EKG channel unit, and the power supply unit.

FIG. 5 shows the signal channel which is preferably an adjustable high gain amplifier with a band-pass filter. The signal detected by the sensors 71 first goes to a high impedance, low noise differential amplifier 101 and 102 and then through a low noise pre-amplifier 104. An analog Chebyshev band-pass filter 105–112 is also utilized to supress noise. The low- and high- cutoff frequencies of the band-pass filter are preferably 100 and 1000 Hz respectively. The filtered signal is then further amplified by another set of 3 stage amplifiers 114–116, yielding an approximate output of 5 volts peak-to-peak. The amplified and filtered signal is then fed into the analog-digital converter 80 (FIG. 4) of the computer through a current driver 117. The signal/noise ration (SNR) may be as low as −40 to −60 dB. The analog band-pass filter 105–112 in the system increases the SNR by 20 to 40 dB; while the overall gain of the entire acoustic aneurysm detector is in the range of 80 to 100 dB. This high gain increases the effect of the thermal noise produced by the elements in the system; which, however, may be easily removed by signal processing techniques (which will be discussed hereinbelow). It will be appreciated that a signal channel of this type will preferably be provided for each sensor 20–26.

FIG. 6 shows the EKG channel which is a combination of analog and logical circuits. It contains input probes 130, 132, a low noise differential amplifier 134 and 136, followed by a 60 Hz notch filter 138 and 139 and two stages of non-inverting amplification 140 and 141. The output 144 of the last state is divided into two paths 145 and 146. One path 145 passes through a peak value detector 150 and 151 and is followed by a low pass filter 152 and 153. Approximately 80% of the filter's output voltage is received through a potentiometer 154 of low pass filter 152 and connected to a comparator 160 as one input. The second path 146 is directly connected to the comparator 160 as another input. The comparator 160 compares the two pathways 145 and 146, and its logical output is differentiated by differentiator 161 and sent to a current driver 162, and then to the computer's programmable clock 164 as a trigger signal for data acquisition.

Referring to FIG. 7, the power supply of the acoustic aneurysm detector will be discussed. This unit 200 will reduce undesired noises created by the interaction between different channels, the 60 cycles, and other burst noises from different power supplies. This unit provides separate power for each channel during system operation and may be connected to a conventional 110 volt power supply 201 to recharge the batteries. The power supply 201 feeds power into the transformer 202, which then feeds the power into four rechargeable 12 volt batteries 206–209. The batteries 206–209 are used as power supplies during the operation of the system, i. e., the "operation mode". The power supply unit enters a rechargeable mode after operation. The two modes are interchanged by a 2×32 switch 210. The diodes 211–214 shown in FIG. 7 are used to avoid the possible circuit burn-out due to battery polarity reverse or battery failure. In the latter case, the diodes serve as fuses. The meter 215 is used to monitor the voltage of each channel.

The output of each signal channel and the output of the EKG channel are connected to the analog to digital converter 80 (FIG. 4) of the computer 29 for digitization. The analog to digital converter 80 simultaneously samples the analog output from each of the eight channels preferably with an adjustable sampling rate of about 3000 samples/second to 7000 samples/second which is higher than the Nyquist rate to avoid aliasing. The time to start the sampling of the signal is first determined by the technician operating the system at "$t_s$", whereas "$t_d$" represents the time interval set-up by the operator as a program parameter and "$t_o$" represents the recording time interval also being a program parameter. FIG. 8(A) represents the EKG signal whereas FIG. 8(B) represents the trigger R-wave from the EKG. FIG. 8(C) is the aneurysmal sound signal whereas FIG. 8(D) is the time window. FIG. 8(E), finally, is the digitized signal.

The analog to digital converter 80 automatically turns on after a predetermined delay time, "$t_d$" determined by the peak value of the R-wave of EKG. The analog to digital converter 80 then turns off after a predetermined observation interval (usually about 300–600 ms) has been reached. The process repeats n times (on FIG. 8, n=3), where n is a predetermined number. A digitized recording is produced by averaging the n consecutive digital sequences. The averaging can increase the SNR by a factor of the square root of "n" because some noises are non-correlated to the systolic period. Selecting "n" at about 3 to 10 is effective to produce satisfactory results.

The suitable computer 29 for use in the present system is a DEC LSl 11/73. This specific system consists of a DEC LSl 11/73 processor having 512 KBytes of memory, a 40 MByte Winchester drive, a 512 KByte floppy disk drive, a programmable clock, and eight channel analog to digital converter 80, a two channel digital to analog converter, a 16 bit digital output word, and four asynchronous communication channels.

FIG. 9 shows the acoustic aneurysm detector 10 as implemented with an Apollo DN 3000 workstation and mounted on a portable cart 250 having wheels 251 and 252 and two other wheels (not shown). The cart 250 has space for the Apollo computer monitor and keyboard 252. The signal receiving units 254 associated with the EKG system (FIG. 6) and the signal receiving units 255–261 of the seven sensors 20–26 (not shown here) are mounted below the computer monitor and keyboard 252. The power supply unit 200 is mounted below the signal receiving units 254–261 and the main computer unit 262 is mounted on the bottom of the cart 250.

The preferred software package preferably consists of a multichannel digitization program associated with the analog to digital converter 80 with adjustable delay intervals, observation intervals, and sampling frequencies.

The digital signals recorded are then processed by a program consisting of Digital Fourier Transform (DFT) spectrum analysis, spectrogram analysis, and band-pass filtered signal analysis.

A DFT spectrum of the recorded signal is computed by Fast Fourier Transform (FFT) of the signal, and the calculation of its magnitude. It is a particularly simple and effective if a narrow band aneurysm signal is present.

Figure 10A:
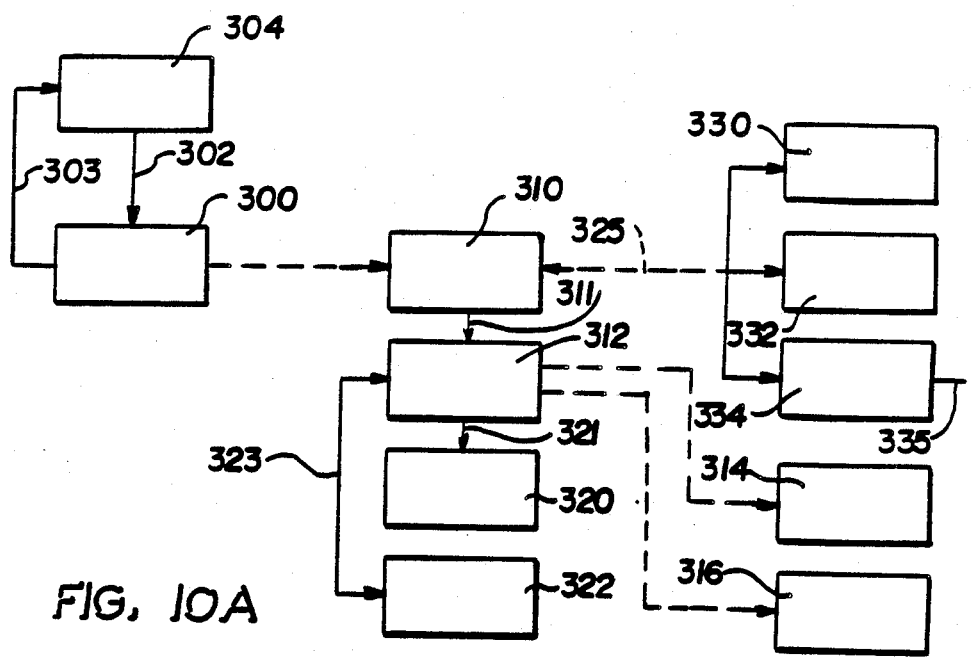
FIGS. 10(A) and 10(B) are flow-charts of a form of the software which can be utilized in the acoustic aneurysm detector.
Figure 10B:
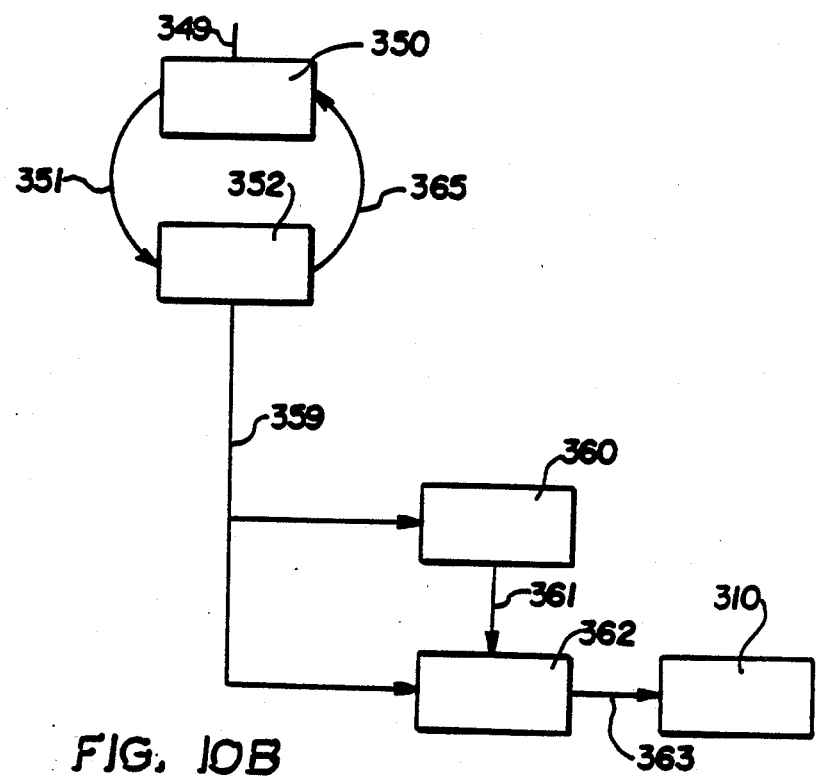

FIGS. 10(A) and 10(B) show a flow-chart of the software utilized in the invention. It will be appreciated that numerous means for accompanying the specific objective will be readily known to those skilled in the art, but a preferable approach will be provided herein.

Referring to FIG. 10(A), the main menu first indicates a directory, NUERO 300 which is in a loop 302–303 with a standard initialization program 304. The NUERO 300 program contains standard programs for building patient records, modifying information, file copying and the like.

The NUERO 300 program calls up the data acquisition program NCDACU 310. This program will be explained in greater detail hereinbelow. This data acquisition program 310 feeds data through line 311 into a standard FFT computation program, SPCANL 312. SPCANL 312 consists of SPECTRO 314, which is a standard FFT routine well known to those skilled in the art, and BANPAS 316 which is a standard band pass filtering program well known to those skilled in the art. This data is then outputted to REVTST 320 through line 321 which allows bringing up test data for review or to PLTTST 322 through line 323 which is a standard plotting package well known to those skilled in the art.

The NCDACU 310 is connected by line 325 to three separate subroutines. The first is ERPRIN 330, which inputs test parameters into the program. The second is ERICLR 332 which is a standard clearing and zeroing data routine. Also, ERICLR 332 initializes the data and display buffers. Finally, ERPCRT 334 generates the Cathode Ray Tube (CRT) display of data through line 335 to a cathode ray tube (not shown).

FIG. 10(B) is the data acquisition software which is associated with the main software shown in FIG. 10(A). Reference number 350 shows a routine CKDONE which is an asynchronous completion routine that starts with a synchronous signal from the EKG channel (FIG. 6) which is sent through lead 349. CKDONE 350 turns the clock on, and when the clock reaches the delay time, "$t_d$" (See FIG. 8(D)) the program sends an interrupt signal to the analog to digital converter 80 (FIG. 4). The analog to digital converter 80 runs the desired number of data points and after this is done, an interrupt signal is sent to another completion routine ADDONE 352 by line 351.

ADDONE 352 takes these data points and sends them to a subroutine RJCT 360 by line 359, which scans the data for "artifacts" which are non-acceptable data points representing high frequency noise such as room noise or loud patient noises such as coughing or sneezing. After the artifacts have been removed, the data is sent by line 361 to a subroutine DWADD 362 which averages the artifact free data and outputs this data back to the main software NCDACU 310 through line 363.

After this has occurred, the program returns to CKDONE 350 by line 365 and the process starts again. For n=3 (as discussed hereinbefore) the data acquisition software will run three times. It will be appreciated that the data acquisition software will run simultaneously with the main software, NCDACU 310.

Referring now to FIGS. 11–17, the output of the software will be discussed. For convenience of reference herein, a "spike" will be considered to exist when there are present high amplitude vibrations within a 50 Hz frequency range and at least two times the amplitude of the intracranial noise. As used herein a "bruit" will be considered to exist when there are present high amplitude vibrations and at least one and one half times the amplitude of the surrounding noise. The existence of an aneurysm can be determined by locating the frequency spikes or bruits on the plot of the spectrum. However, in some cases where the bandwidth of the aneurysmal signal is not narrow enough and the frequency characteristics vary with time, the DFT spectrum method may fail to detect the aneurysm. Because of this, the spectrogram is performed in addition to the segmented DFT analysis. Thus, preferably, the analysis is done by first (a) looking at change in frequency over time, then (b) by doing FFT analysis, and then finally, (c) a spectrogram analysis. While it is preferred to use all three in analyzing the sound from the aneurysm, only one can be used, if desired. In general, it will be preferred to use step (a) in all instances.

The spectrogram is a 2-dimensional image produced from a 1-dimensional recorded signal. Its x and y axes are time and frequency respectively, and the z axis (which may be represented by the gray-levels of the image) is the strength of energy emitted by the vibration of an aneurysm at a particular time and frequency. Such an approach is known to those skilled in the art and is disclosed in Rabiner et al. Digital Processing of Speech Signals, Prentice Hall Inc. (1978).

After the smoothing with a window function, the tendency of frequency changes can be clearly seen.

The band-passes filtered signal analysis is also utilized for providing additional information to detect the presence of the aneurysm. The signal is filtered by ten consequent frequency bands. The energy ratio of each frequency band and the total energy is computed and the ten filtered signals are plotted. By examining the plots, the time signatures of the aneurysmal signal can be located. Using the computed energy ratio, the strength of the aneurysmal signal can be estimated.

Figure 11:
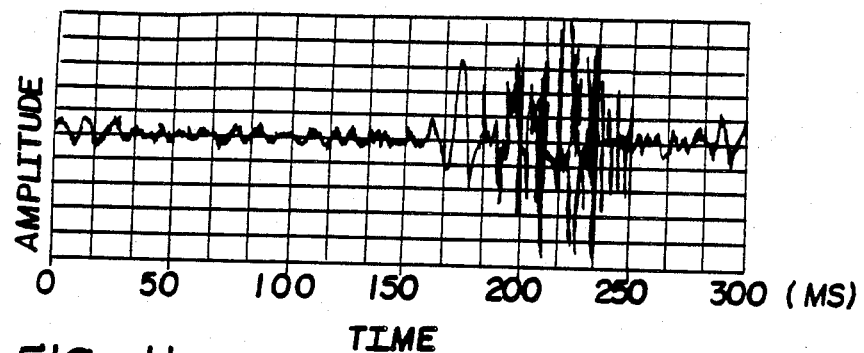
FIG. 11 is a time plot of the sound from a experimental aneurysm.
Figure 12:
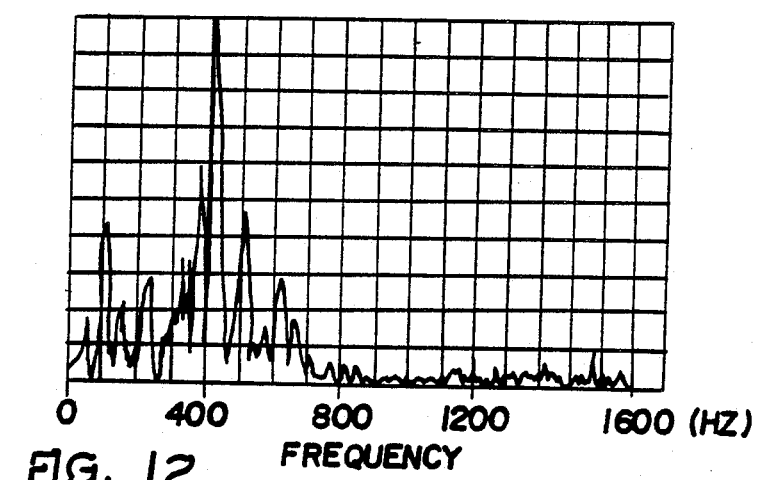
FIG. 12 shows a DFT spectrum of the sound of FIG. 11.

A typical time signature of the signal recorded intraoperatively from an experimental aneurysm in a dog is shown in FIG. 11. The DFT spectrum and spectrogram of the signal shown in FIG. 11 are shown in FIG. 12 and FIG. 13 respectively.

Observing FIG. 11 in the time period between 175 ms to about 250 ms, there is a greatly increased frequency. This is shown also by looking at the FFT analysis in FIG. 12 which shows increased strength of energy emitted in the 100 to 700 Hz range with a maximum occurring at 400 Hz. Finally, it is noted that the spectrogram in FIG. 13 shows distinct regions of increased magnitude. All of these tests show the probable existence of an aneurysm.

Figure 14:
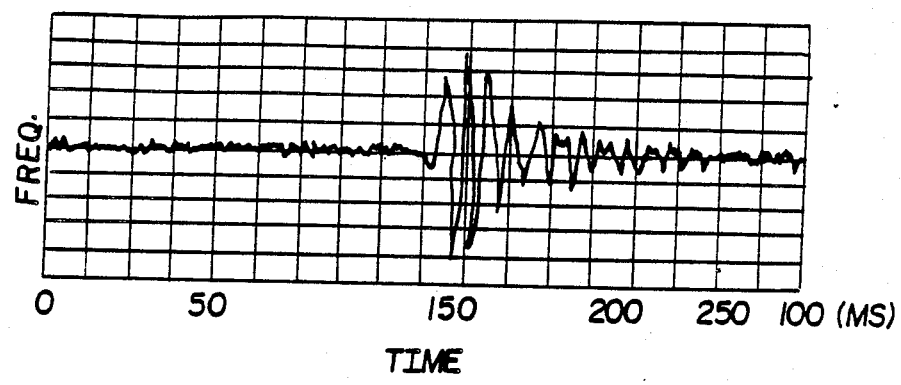
FIG. 14 is a time plot of the sound from the carotid artery in a dog before the creation of the aneurysm.
Figure 15:
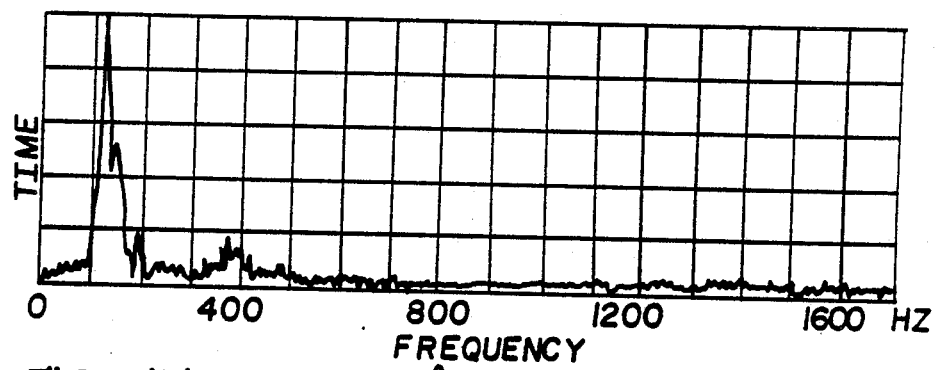
FIG. 15 shows a DFT spectrum of the sound of FIG. 14.
Figure 16:
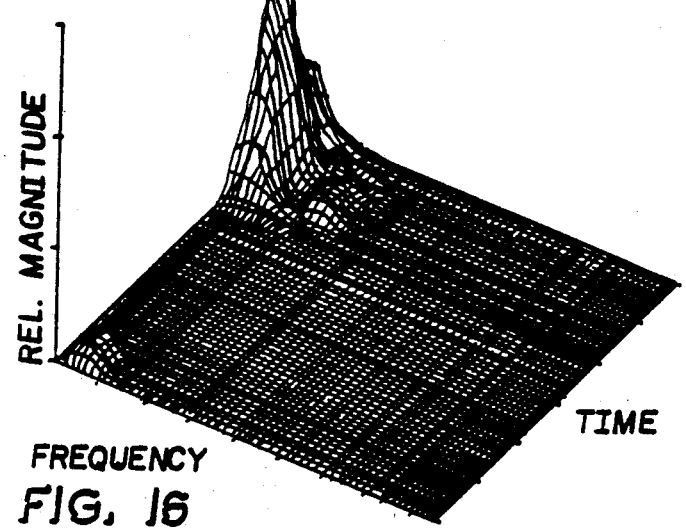
FIG. 16 shows a spectrogram of the sound of FIG. 14.

For the purpose of comparison, a typical record of a carotid signal, its DFT spectrum and spectrogram are also shown in FIGS. 14–16. The significant differences in time signatures, frequency spectra, and spectrograms can be clearly seen.

Figure 13:
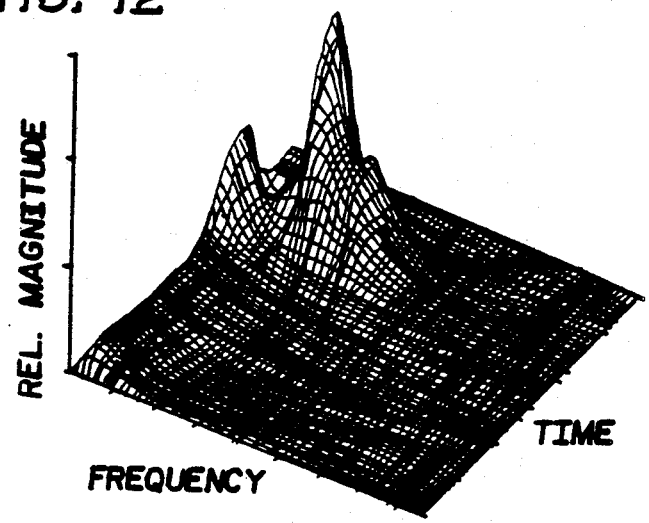
FIG. 13 shows a spectrogram of the sound of FIG. 11.

In examining the spectrograms of the aneurysmal signal shown in FIG. 13, a low-high-low pattern with a systolic period demonstrating a time-varying frequency characteristic is seen. The vibration appears not quite sinusoidal, indicating the complexity of the aneurysmal signal. In contrast, the major frequencies of the carotid signal shown in FIG. 16 were found to be very sinusoidal resulting in a sharp spike along the frequency axis. This difference in contour provides an indication of the presence of an aneurysm.

Figure 17F:
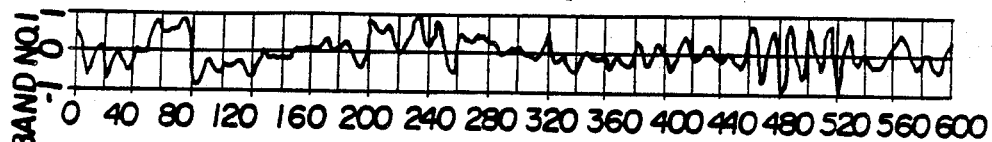
Figure 17G:
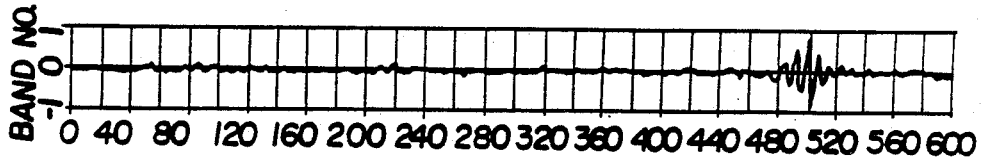
Figure 17H:
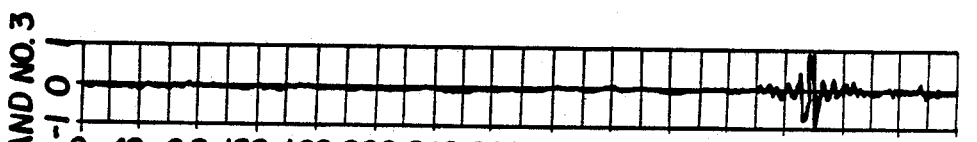
Figure 17I:
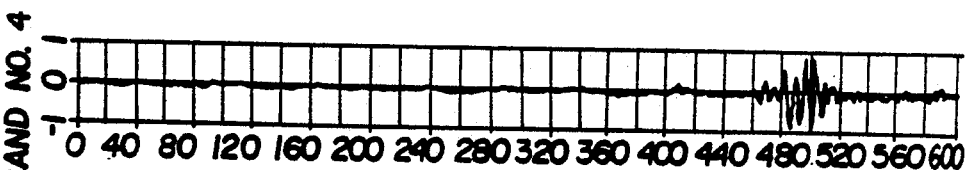
Figure 17J:
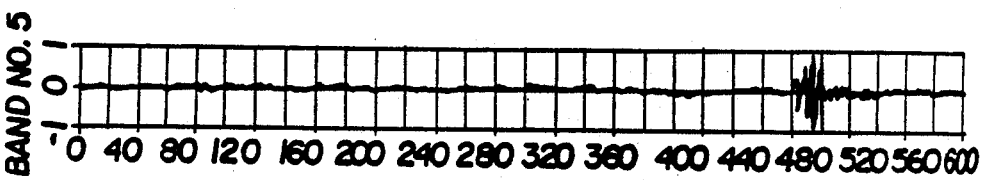
Figure 17K:
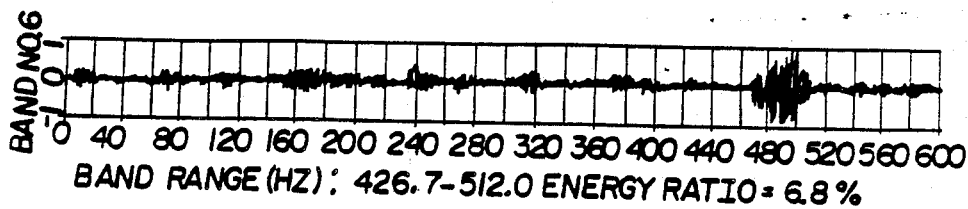
Figure 17L:
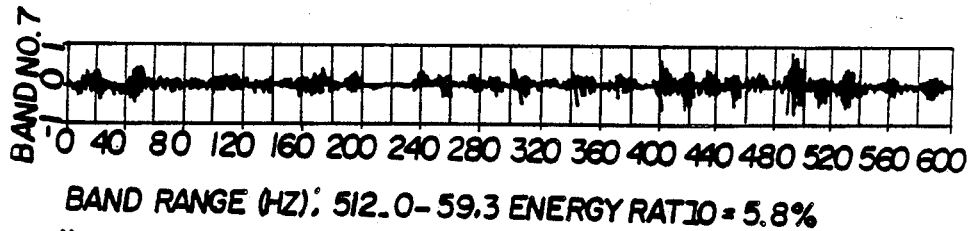
Figure 17M:
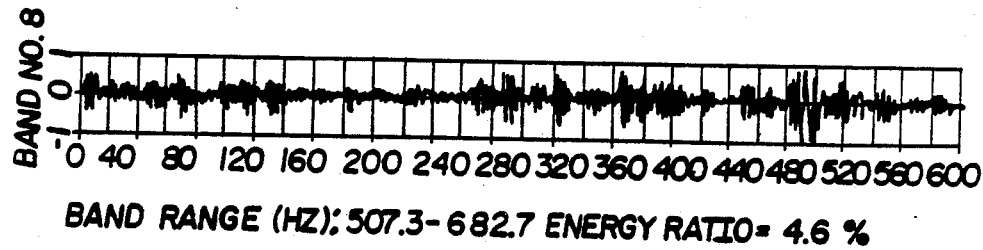
Figure 17N:
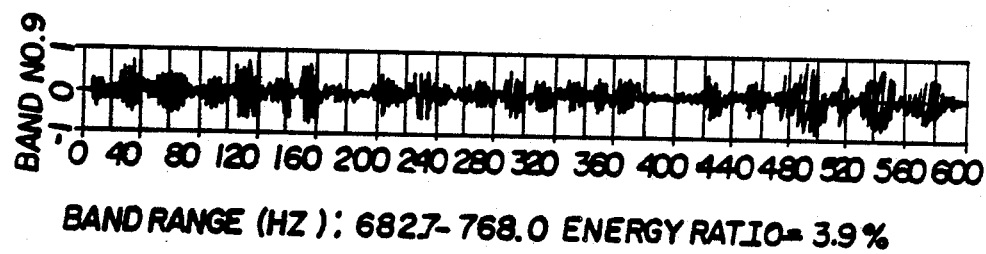
Figure 17O:
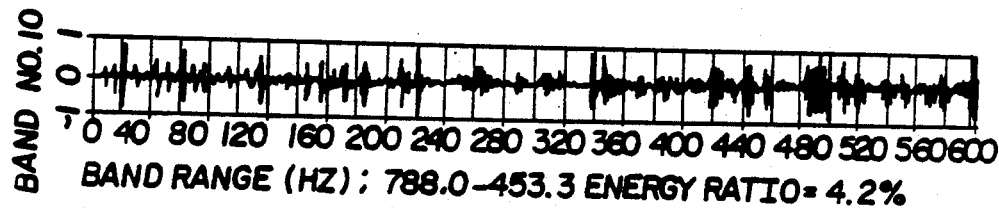

FIGS. 17(A)–17(0) show a complete record of the aneurysmal signal recorded noninvasively by using the acoustic aneurysm detector from a sixty-five year old female with a 2×2×2 cm aneurysm at the vertebral/basilar junction. From the spectrogram FIG. 17(E), it can be seen that there is a peak at a low frequency, with 3 other resonant frequency peaks at 250, 350, and 400 Hz. These features cannot be seen clearly from the time signature FIG. 17(A) and frequency plots FIG. 17(C), showing the advantages of utilizing the spectrogram in signal analysis. The band-pass filters FIGS. 17(F-O) provide additional information about the aneurysmal signal, showing that the acoustic aneurysmal signal is distributed in the frequency bands FIGS. 17(G-K) and that 46% of the signal energy is concentrated in bands 2 and 3.

It will be appreciated that, the method of the invention involves determination of the probable existence of an aneurysm by providing an acoustic aneurysm detector comprising sensor means as described hereinabove, placing the sensors on a patient for receiving sound from the patient, converting the sound into responsive electrical signals by the electronic means, filtering and amplifying the responsive electrical signals by the electronic means to create processed electrical signals, delivering the processed electrical signal to the analysis means and outputting an indication of the frequency of the sound over a specified time range, whereby presence or absence of an aneurysm in a patient may be detected.

It will further be appreciated that an acoustic aneurysm detector is provided which is comprised of hydrophone sensors means, electronic means, and data analysis means which can effectively noninvasively determine the presence or absence of an aneurysm.

While for convenience of disclosure, reference has been made herein to use in detection of aneurysms in the cranium, it will be appreciated that aneurysms in other parts of the body can be detected by the accoustic aneurysm detector.

Whereas a particular embodiment of the invention has been described, for purposes of illustration, it would be evident to those skilled in the art that numerous variations of the details may be made without departing from the invention as defined in the appended claims.

We claim:

1. An acoustic intracranial aneurysm detector consisting of
    as plurality of hydrophone sensors adapted to be in contact with a patient for receiving sound emanating from said patient and for converting the sound to be responsive electronic signals, means for adjustably positioning said sensors in contact with the patient's head,
    electronic means for filtering and amplifying the responsive electric signals to create processed electrical signals, and
    analysis means operatively associated with said electronic means for receiving said processed electrical signals and for simultaneously providing an output indication of the frequency and relative magnitude of said sound at each of a plurality of time intervals within a cardiac cycle of said patient, whereby the presence or absence of an aneurysm in said patient can be detected.

2. The detector of claim 1, wherein
    said plurality of hydrophone sensors includes a hydrophone sensor for monitoring room noise.

3. The detector of claim 2, wherein said means for positioning is further adapted to position one of said hydrophone sensors on said patient's neck.

4. The detector of claim 3, wherein
    said hydrophone sensors are at least six in number.

5. The detector of claim 4, wherein five of said hydrophone sensors are adapted to be positioned for monitoring said sound from said aneurysm and one of said hydrophone sensors is adapted to be positioned for monitoring biological noise.

6. The detector of claim 1, including
wherein said positioning means includes helmet-like means for mounting said hydrophone sensors and for positioning on said patient's head.

7. The detector of claim 6, including
said helmet-like means having a central hub and a plurality of fingers which have disposed on their ends said hydrophone sensors.

8. The detector of claim 7, including
said fingers having adjustment means, whereby said hydrophone sensors are adapted to be in contact with said patient's head.

9. The detector of claim 8, including
said adjustment means including tongue and groove means which are slidable relative to each other.

10. The detector of claim 9, including
said helmet-like means having five fingers with one said hydrophone sensor associated with each.

11. The detector of claim 1, including
said electronic means having a plurality of signal channel means and power supply means.

12. The detector of claim 11, including
said signal channel means having an EKG channel and a plurality of sensor channel means.

13. The detector of claim 12, including
said sensor channel means being provided for each of said hydrophone sensors.

14. The detector of claim 13, including
said sensor channel means having filter means and amplifier means for converting said responsive electrical signals into said processed electrical signals for input into said analysis means.

15. The detector of claim 1, including
said analysis means comprising analog to digital converter means for digitization of said processed electrical signals and computer means for receiving, analyzing and outputting said indication of the frequency of said digitized and converted sound signals.

16. The detector of claim 15, including
said computer means having multichannel digitization software for analyzing and outputting said digitized and converted sound.

17. The detector of claim 16, including
said digitization software outputting a frequency versus time indication of said sound.

18. The detector of claim 17, including
said software having means capable of presenting output information which presents a visual display which enables a viewer to determine whether a bruit or a spike exists.

19. The detector of claim 18, including
said software having means capable of outputting a Fourier Fast Transform of said sound.

20. The detector of claim 19, including
said software having means capable of outputting a spectrogram analysis of said sound.

21. The detector of claim 18, including
said software having means capable of outputting a spectrogram analysis of said sound.

22. The detector of claim 21, including
said software having means capable of outputting a Fourier Fast Transform of said sound.

23. A method of detecting the presence or absence of an aneurysm in a patient comprising the steps of
providing an acoustic aneurysm detector including a plurality of hydrophone sensors an electronic means, and analysis means,
mounting said hydrophone sensors means on said patient to receive a sound from said patient,
converting said sound by said hydrophone sensors to responsive electrical signals,
amplifying and filtering said responsive electrical signals by said electronic means to create processed electrical signals,
delivering said processed electrical signals to said analysis means, and
outputting a simultaneous indication of the frequency and relative magnitude of said sound at each of a plurality of time intervals within a cardiac cycle of said patient, whereby the presence or absence of said aneurysm in a patient may be detected.

24. The method of claim 23, including
maintaining intimate contact of said hydrophone sensors with said patient.

25. The method of claim 24, wherein said mounting step includes
providing helmet-like means to hold said hydrophone sensors in intimate contact with said patient's head.

26. The method of claim 23, including
maintaining said patient in a reclining position.

27. The method of claim 23, including
processing said processed electrical signals by a Fast Fourier Transform and outputting a Digital Fourier Transform of said processed electrical signals.

28. The method of claim 23, including
processing said processed electrical signals by a spectrogram analysis and outputting a spectrogram of said processed electrical signals.

29. A sensor device for use in determining the presence or absence of an aneurysm in a patient comprising a plurality of hydrophone sensors
a helmet-like device adapted to be worn on said patient's head including means for receiving said plurality of hydrophone sensors said hydrophone sensors being received within said receiving means such that said sensors are adapted to be in contact with said patient's head, and
said helmet-like device having a central hub, and wherein said receiving means includes a plurality of fingers which have disposed on their ends said hydrophone sensors.

30. The detector of claim 29, including
said fingers having adjustment means, whereby intimate contact of said hydrophone, sensors with said patient's head is maintained.

31. The detector of claim 30, including
said adjustment means including tongue and groove means.

32. The detector of claim 31, including
said plurality of finger comprises five fingers with a said hydrophone sensors associated with each of said five fingers.

* * * * *